United States Patent
Fischer et al.

(10) Patent No.: US 8,184,770 B2
(45) Date of Patent: May 22, 2012

(54) X-RAY ACQUISITION METHOD AND DEVICE FOR STEREOTACTIC BIOPSY

(75) Inventors: Daniel Fischer, Erlangen (DE); Michael Hall, Nuremberg (DE); Carina Hofmann, Erlangen (DE); Katrin Johansson, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 522 days.

(21) Appl. No.: 12/354,414

(22) Filed: Jan. 15, 2009

(65) Prior Publication Data

US 2009/0190819 A1     Jul. 30, 2009

(30) Foreign Application Priority Data

Jan. 28, 2008   (DE) .......................... 10 2008 006 358

(51) Int. Cl.
    *G01N 23/04*      (2006.01)
    *G06K 9/00*      (2006.01)
    *A61B 6/04*      (2006.01)

(52) U.S. Cl. ............................. 378/62; 382/132; 378/37

(58) Field of Classification Search ................. 378/4, 19, 378/37, 38, 57, 62, 65; 382/128, 130–132
See application file for complete search history.

(56) References Cited

U.S. PATENT DOCUMENTS

| | | | |
|---|---|---|---|
| 6,028,912 A * | 2/2000 | Navab | 378/62 |
| 6,970,585 B1 * | 11/2005 | Dafni et al. | 382/131 |
| 7,313,224 B1 | 12/2007 | Saunders | |
| 2004/0171933 A1 * | 9/2004 | Stoller et al. | 600/427 |
| 2007/0076937 A1 | 4/2007 | Spahn | |
| 2007/0195928 A1 * | 8/2007 | Lozano Fantoba et al. | 378/62 |
| 2008/0045833 A1 * | 2/2008 | Defreitas et al. | 600/429 |

* cited by examiner

*Primary Examiner* — Irakli Kiknadze
(74) *Attorney, Agent, or Firm* — Schiff Hardin LLP

(57) ABSTRACT

In a method and an associated device for generation of digital x-ray image exposures of an examination subject with an x-ray source and a digital x-ray detector for a stereotactic biopsy, wherein, for one or more x-ray image acquisitions of the examination subject with a biopsy device, acquisition and image processing parameters are used that have been determined from an x-ray image exposure of the examination subject without the biopsy device (7). The influences that are disruptive for an optimal x-ray image, for example of metallic biopsy devices, can thereby be avoided.

18 Claims, 2 Drawing Sheets

X-RAY ACQUISITION METHOD AND DEVICE FOR STEREOTACTIC BIOPSY

BACKGROUND OF THE INVENTION

1. Field of the Invention

The invention concerns a method for generation of digital x-ray image exposures and an x-ray image acquisition device for implementing such a method.

2. Description of the Prior Art

X-ray image acquisitions of the human breast normally ensue with mammography apparatuses. Medical examinations of the soft tissue of the human breast with x-ray radiation that serve for early detection of breast cancer can be conducted with a mammography apparatus. The breast to be examined is clamped between a subject table and a compression plate that can be displaced against the subject table. An x-ray image acquisition subsequently ensues with an exposure unit fashioned as an x-ray radiator. For this purpose, an x-ray detector is typically integrated into the subject table. Radiation known as soft x-ray radiation, in the range below 50 kV, is used in the acquisition.

Modern mammography apparatuses (for example the "MAMMOMAT Novation" that is commercially available from Siemens Healthcare) have a base body fashioned as a support and a curved apparatus arm projecting from the support, at the free end of which is arranged a radiation source. The apparatus arm is formed as a plate structure and is connected in a torque-resistant manner with a horizontal rotation axis of the mammography apparatus, so that the radiation source can be pivoted by 360° around an isocenter. A subject table that can be pivoted by 360° around the isocenter is supported on the apparatus arm by a revolving joint.

The mammography apparatus is typically used for examinations known as screening examinations in which the exposure unit is located in a 0° position, with the exposure unit and the subject table arranged opposite one another in the longitudinal direction. Furthermore, the mammography apparatus is also fashioned for a stereo image examination in which the breast is exposed from two different angles. Here the exposure unit is pivoted by +/−10° or by +/−15° from the rest position around the horizontal axis given a stationary subject table. Furthermore, often examinations known as tomosynthesis examinations are also possible with the mammography apparatus, in which the exposure unit travels continuously over a relatively large angle range, for example in an angle range from +/−25° around the horizontal axis given a stationary subject table. Furthermore, an MLO presentation (medio-lateral-oblique) is possible. In this examination, the exposure unit is normally found in a 45° position, and the subject table follows the exposure unit so that subject table and exposure unit are always aligned in the same position and at the same distance relative to one another. The mammography apparatus therefore allows the acquisition of the breast to be examined in standard presentations such as what is known as the cranio-caudal (CC) or medio-lateral-oblique (MLO) presentation, for example.

The "MAMMOMAT Novation" enables a stereotactic biopsy of the human breast in cooperation with the "Opdima" digital biopsy and target acquisition system by the applicant. In stereotactic biopsy a tissue sample of the human breast is extracted and subsequently histologically examined.

For a biopsy, the breast is compressed in the mammography apparatus with a compression plate specially fashioned for the biopsy and is fixed in this position. A first x-ray image acquisition (known as the overview acquisition) subsequently ensues in order to determine whether the tumor or another tissue part to be biopsied lies within a recess of the compression plate.

All following acquisitions ensue in pairs from two different directions, as described above. They are therefore designated as stereo acquisitions. From the first stereo acquisition, the point in the breast that is to be biopsied is marked, and the required penetration position, penetration direction and penetration depth of a biopsy needle are calculated from this. The biopsy needle is subsequently inserted into the breast at the calculated point with the aid of a biopsy device, and additional stereo exposures are shot to monitor the position of the needle tip.

The biopsy needle and biopsy needle mount are therefore imaged in these additional stereo exposures. Both overlap a large portion of the tissue surface of the breast in the x-ray image exposures. Therefore, automatic contrast and brightness adaptations which are based on these exposures deliver no constant image quality. Moreover, no automatic exposure correction (AEC) is possible in these exposures.

In most cases, the x-ray image acquisition is manually windowed by an operator in order to achieve a satisfactory image quality. The duration of an examination is thereby unnecessarily extended, which is uncomfortable for the patient and increases the costs of a biopsy.

In "Opdima", metal artifacts are segmented via a histogram analysis. This segmented region can then be excluded for a contrast and brightness adaptation.

SUMMARY OF THE INVENTION

An object of the invention is to provide an additional method and an associated device which deliver an x-ray image exposure with improved image quality for stereotactic biopsy.

According to the invention, in the method for generation of digital x-ray image exposures of an examination subject (for example the female breast) with an x-ray source and a digital x-ray detector for a stereotactic biopsy for one or more x-ray image acquisitions of the examination subject with a biopsy device, acquisition and image processing parameters are used that have been determined from a previously generated x-ray image exposure of the examination subject without the biopsy device. The biopsy device can have a biopsy needle and a biopsy needle mount, wherein only the biopsy needle is inserted into the examination subject.

This advantageously avoids interfering influences, for example from metallic biopsy devices that can prevent an optimal x-ray image from being achieved.

In an embodiment, the method can include the steps of generating an overview exposure of the examination subject using first acquisition and image processing parameters, storing of the first acquisition and image processing parameters, generating a first stereo image exposure of the examination subject with the first acquisition and image processing parameters, determining the position of a subject to be biopsied, inserting a biopsy needle into the examination subject, and generating at least one additional stereo image exposure of the examination subject using the first acquisition and image processing parameters.

The image quality of x-ray exposures with a biopsy device can thereby be improved.

In a further embodiment, the method can include the steps of generating an overview exposure of the examination subject, generating a first stereo image exposure of the examination subject using second acquisitioning image processing parameters, storing the second acquisition and image processing parameters, determining the position of a subject to be biopsied, inserting a biopsy needle into the examination subject, and generating at least one additional stereo image exposure of the examination subject using the second acquisition and image processing parameters.

The image quality of x-ray image exposures with a biopsy device is also improved in this embodiment.

In another embodiment, the first acquisition parameters can be determined from an overview exposure that was acquired with the aid of an automatic exposure correction.

In another embodiment, the second acquisition parameters can be determined from a first stereo image exposure that was acquired with the aid of an automatic exposure correction.

This offers the advantage that an automatic exposure correction (AEC) can be used.

In a further embodiment, the first and the additional stereo image exposures can respectively comprise two x-ray image exposures which are acquired from different angles of the x-ray source.

Spatial position determinations of objects in the examination subject are thereby easily possible.

In another embodiment, the first or second acquisition parameters are each predeterminable values for the x-ray source voltage and x-ray source amperage times the duration of the exposure (mAs).

The exact setting of the exposure of the x-ray image exposures is advantageous for this purpose.

In a further embodiment, the first or second image processing parameters can respectively comprise predeterminable values for contrast and brightness adaptation.

The image processing of the x-ray image exposures can therefore be optimized.

According to the invention, the device for generation of digital x-ray images of an examination subject for a stereotactic biopsy comprises an x-ray source and a digital x-ray detector as well as a control and evaluation unit to detect the digital x-ray images and a memory unit to store acquisition and image processing parameters. The control and evaluation unit is fashioned such that the acquisition and image processing parameters of an x-ray acquisition of the examination subject that are stored in the memory unit for x-ray image acquisitions with a biopsy device are used without the biopsy device.

This entails the advantage that the influences that are disruptive for an optimal x-ray image (for example from metallic biopsy devices) can be avoided.

In an embodiment, the acquisition and image parameters can comprise predeterminable values for the x-ray source voltage and x-ray source amperage times the duration of the exposure (mAs) and/or predeterminable values for contrast and brightness adaptation.

An exact setting of the exposure of the x-ray image exposures can thereby ensue and the image processing of the x-ray image exposures can be optimized.

In an additional embodiment, the x-ray image exposure without the biopsy device can be an overview exposure, a stereo image exposure or a preliminary exposure (for example normal mammography exposure) of the examination subject.

The acquisition and image processing parameters of an x-ray image acquisition that is required anyway can be used for this purpose.

According to the invention, a mammography apparatus is also specified with a device according to the invention to implement the method according to the invention.

The possibility for use in mammography is additionally advantageous.

According to the invention, a computer-readable medium is encoded with programming instructions that implement a method according to the invention when the computer program is executed in a control unit of a device according to the invention.

DESCRIPTION OF THE PREFERRED EMBODIMENTS

Figure 1:
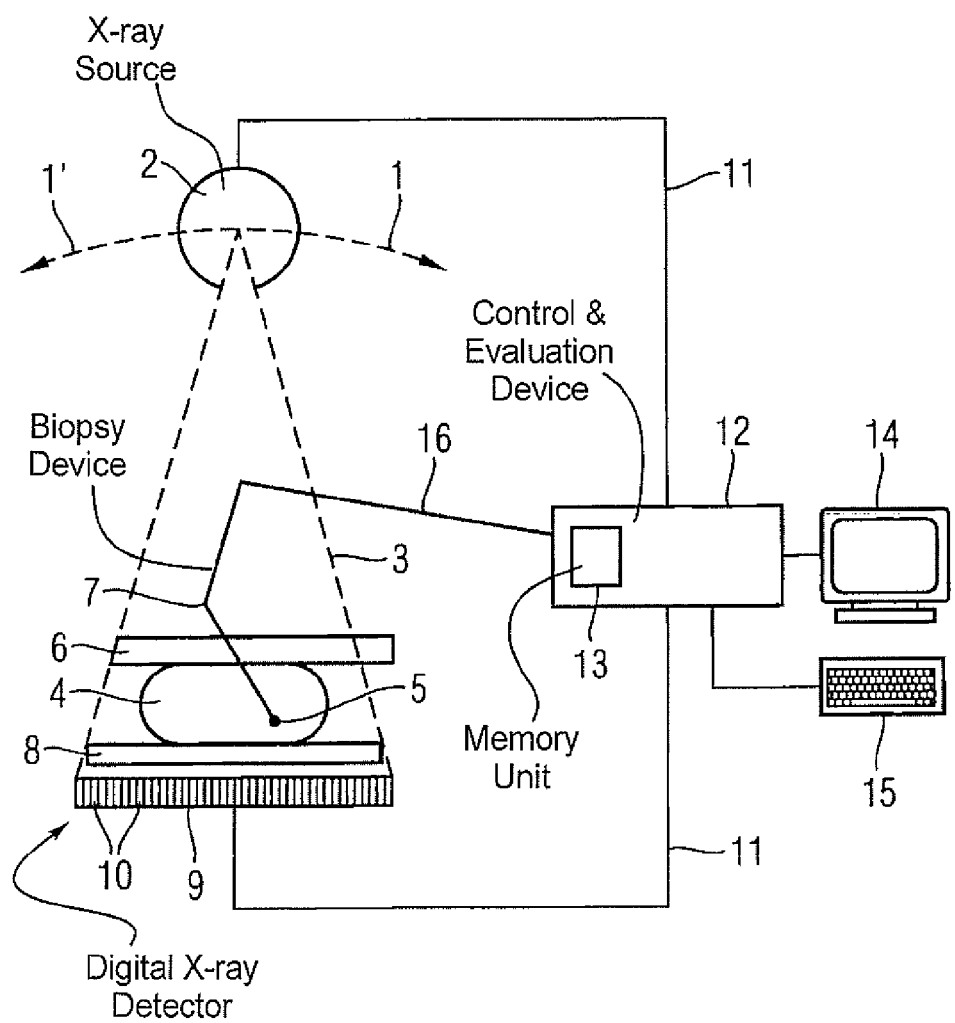
FIG. 1 is a block diagram of a device for generating digital x-ray images in accordance with the invention.

According to FIG. 1, a device to generate a digital x-ray image (for example a mammography apparatus) comprises an x-ray source 2 to generate x-rays 3 that pass through an examination subject 4. The examination subject 4 in the example is a female breast that is embedded between a compression plate 6 and a patient support table 8. The x-rays 3 passing through the examination subject 4, the compression plate 6 and the patient support table 8 are received by a large-area digital x-ray detector 9 that is composed of a number of individual detectors 10 arranged in a matrix-like array. A scattered-ray grid (not shown) can additionally be arranged in front of the x-ray detector 9 to suppress scatter radiation.

The control of the x-ray source 2 as well as of its operating and acquisition parameters ensues via control signals in the control lines 11, which control signals are generated by the control and evaluation device 12. The acquisition parameters required to generate a complete x-ray image can be set by the user with the aid of input and display elements 14, 15 (symbolically illustrated in the example by a keyboard 15 and a monitor 14). Alternatively, the parameters can be automatically set. The acquisition then consists of a preliminary image (also called a preshot) that is acquired with a partial dose and the complete x-ray image that is shot with the full dose.

An automatic evaluation of the preliminary image acquired with the partial dose ensues in the control and evaluation device 12 after the preshot with the methods as they are known for automatic exposure control (AEC) in order to determine in this way the dose required to generate the x-ray image. A complete overview exposure is then acquired with this dose given otherwise unchanged acquisition parameters. The image processing parameters are available after processing the image. The acquisition and image processing parameters are cached in a memory unit 13 for a further use.

Two x-ray images are subsequently acquired with pivoted x-ray source 2, for which the x-ray source 2 is brought into positions 1 and 1'. The dose values and image processing parameters determined in the overview image are advantageously used for this, what is known as a stereo image acquisition.

The object 5 (for example a tumor) is now marked in these acquired stereo images automatically or by medical personnel, and the geometric position data of the object 5 are determined in the control and evaluation unit 12.

For example, a biopsy needle with mounting device is subsequently introduced into the examination subject at the position of the object 5 with the aid of a biopsy device 7. This can ensue manually or (preferably) automatically. The control in this cases ensues via the control and evaluation unit 12. The control impulses are supplied to the biopsy device 7 via a connection line 16.

An additional stereo image is now acquired to monitor the position of the tip of the biopsy needle. For this the acquisition and image processing parameters stored in the memory unit 13 are used. An automatic exposure correction (AEC) can thereby be foregone, which would otherwise lead to too high a dose as a result of the large metal surfaces in the image. Moreover, the image processing parameters calculated from this exposure would lead to an unsatisfactory contrast and brightness adaptation. The use of stored acquisition and image processing parameters is possible since the tissue composition and the thickness of the examination subject matter 4 essentially do not change during the examination time period. In spite of the use of the same acquisition and image processing parameters, it is therefore ensured that the grey values of various x-ray image exposures do not significantly deviate from one another, and thus the contrasts and brightnesses remain the same.

Figure 2:
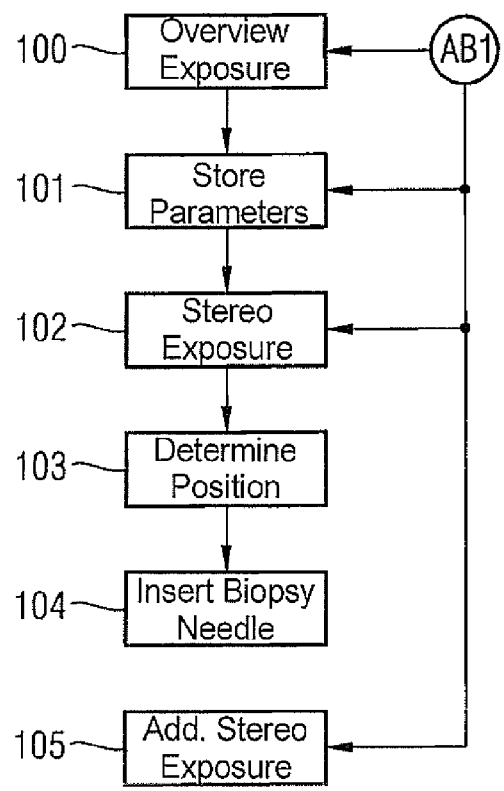
FIG. 2 is a flowchart of a first embodiment of a method in accordance with the present invention.

FIG. 2 schematically shows the temporal workflow of a method according to the invention, wherein an overview exposure of the examination subject is generated in Step 100 with first acquisition and image processing parameters AB1; the first acquisition and image processing parameters AB1 are stored in the following Step 101; a first stereo image exposure of the examination subject is generated with the first acquisition and image processing parameters AB1 in Step 102; the position of an object to be biopsied is localized and determined in a next Step 103; a biopsy needle is introduced into the examination subject in Step 104; and at least one additional stereo image exposure of the examination subject is generated with the first acquisition and image processing parameters AB1 in a concluding Step 105.

Figure 3:
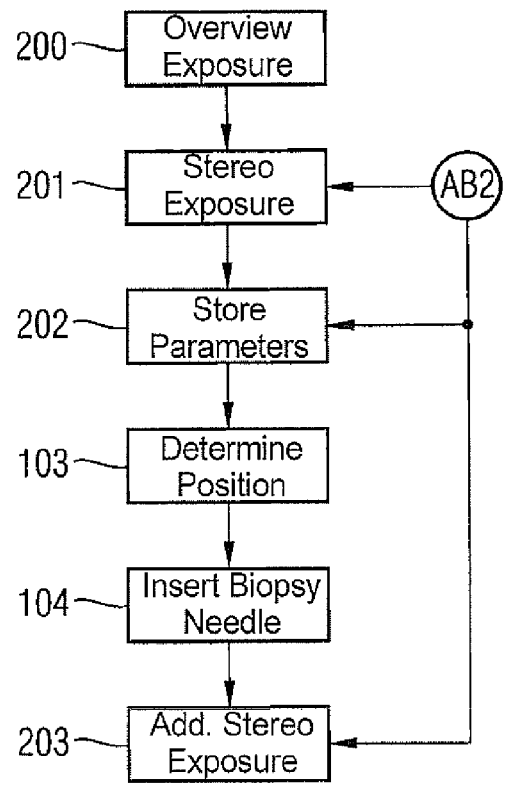
FIG. 3 is a flowchart of a second embodiment of a method in accordance with the present invention.

FIG. 3 schematically shows the temporal workflow of an additional method according to the invention, wherein an overview exposure of the examination subject is generated in Step 200; a first stereo image exposure of the examination subject is generated with second acquisition and image processing parameters AB2 in subsequent Step 201; The second acquisition and image processing parameters AB2 are stored in Step 202; the position of an object to be biopsied is localized and determined in a next Step 103; a biopsy needle is introduced into the examination subject in Step 104; and at least one additional stereo image exposure of the examination subject is generated with the second acquisition and image processing parameters AB2 in a concluding Step 203.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating digital x-ray image exposures of an examination subject comprising:
   irradiating an examination subject with x-rays from an x-ray source having a field of view that encompasses a biopsy device interacting with the subject;
   detecting x-rays from said x-ray source attenuated by the subject and by said biopsy device with a digital x-ray detector;
   determining image acquisition and image processing parameters that were used for an x-ray image exposure of the subject without the presence of the biopsy device; and
   generating an x-ray image of the subject interacting with the biopsy device using said image acquisition and image processing parameters.

2. A method as claimed in claim 1 comprising:
   generating an overview of the examination subject with said image acquisition and image processing parameters;
   storing said image acquisition and image processing parameters;
   generating a first stereo image exposure of the examination subject using the stored image acquisition and image processing parameters;
   determining a position of the subject;
   inserting a biopsy needle of the biopsy device into the subject;
   generating at least one additional stereo image exposure of the subject using the stored image acquisition and image processing parameters.

3. A method as claimed in claim 2 comprising determining said image acquisition parameters from an overview exposure acquired using an automatic exposure correction, and determining said image processing parameters from processing said overview exposure.

4. A method as claimed in claim 3 comprising determining said acquisition parameters from a preshot of said overview exposure.

5. A method as claimed in claim 2 comprising forming said first stereo image exposure and said additional stereo image exposure from two x-ray image exposures acquired with said x-ray source at respectively different angles.

6. A method as claimed in claim 2 comprising employing, as said image acquisition parameters, a voltage of said x-ray source and a product of a current of said x-ray source and a duration of exposure of the subject with said x-rays emitted by said x-ray source.

7. A method as claimed in claim 2 comprising employing, as said image processing parameters, predetermined values for contrast and brightness adaptation.

8. A method as claimed in claim 1 comprising:
   generating an overview exposure of the subject;
   generating a stereo image exposure of the subject using said image acquisition and image processing parameters;
   storing said image acquisition and image processing parameters;
   determining a position of the subject;
   inserting a biopsy needle of the biopsy device into the subject; and
   generating at least one additional stereo image exposure of the subject using said image acquisition and image processing parameters.

9. A method as claimed in claim 8 comprising acquiring said first stereo image exposure using an automatic exposure correction, and determining said image acquisition parameters from said first stereo image exposure acquired with said automatic exposure correction, and determining said image processing parameters from processing said overview exposure.

10. A method as claimed in claim 9 comprising determining said image acquisition parameters from a preshot of said first stereo image exposure.

11. A method as claimed in claim 8 comprising forming said first stereo image exposure and said additional stereo image exposure from two x-ray image exposures acquired with said x-ray source at respectively different angles.

12. A method as claimed in claim 8 comprising employing, as said image acquisition parameters, a voltage of said x-ray source and a product of a current of said x-ray source and a duration of exposure of the subject with said x-rays emitted by said x-ray source.

13. A method as claimed in claim 8 comprising employing, as said image processing parameters, predetermined values for contrast and brightness adaptation.

14. A device for generating digital x-ray images of a subject comprising:
- an x-ray source that emits an x-ray beam that irradiates an examination subject;
- a biopsy device configured to interact with the subject;
- a digital x-ray detector that detects x-rays from said x-ray source attenuated by said subject and by said biopsy device interacting with the subject, and that emits digital data corresponding to the detected, attenuated x-rays;
- a memory in which image acquisition and image processing parameters are stored for an exposure of the subject acquired without interaction with the biopsy device; and
- a control and evaluation unit supplied with said digital data from said x-ray detector and having access to said memory, said control and evaluation unit being configured to generate an x-ray image of the subject interacting with the biopsy device using said image acquisition and image processing parameters stored in said memory.

15. A device as claimed in claim 14 wherein said memory contains predetermined values for a voltage of said x-ray source and a product of a current of said x-ray source and a duration of irradiation of the subject as said image acquisition parameters, and predetermined values for contrast and brightness adaptation as said image processing parameters.

16. A device as claimed in claim 14 wherein said x-ray source and said digital x-ray detector are configured to acquire an image of the examination subject without interaction with said biopsy device selected from the group consisting of overview exposures, stereo image exposures, and pre-shot exposures, and wherein said image acquisition parameters and said image processing parameters are obtained from said image acquired with said x-ray source and said digital x-ray detector without interaction with said biopsy device.

17. A mammography apparatus comprising:
- a platform and a compression device configured to hold and compress a female breast, as an examination subject;
- an x-ray source that emits an x-ray beam that irradiates the examination subject;
- a biopsy device configured to interact with the examination subject;
- a digital x-ray detector that detects x-rays from said x-ray source attenuated by said examination subject and by said biopsy device interacting with the examination subject, and that emits digital data corresponding to the detected, attenuated x-rays;
- a memory in which image acquisition and image processing parameters are stored for an exposure of the examination subject acquired without interaction with the biopsy device; and
- a control and evaluation unit supplied with said digital data from said x-ray detector and having access to said memory, said control and evaluation unit being configured to generate an x-ray image of the examination subject interacting with the biopsy device using said image acquisition and image processing parameters stored in said memory.

18. A non-transitory, computer-readable storage medium encoded with programming instructions, said medium being loadable into a control unit that operates a device for generating digital x-ray exposures of a subject, having an x-ray source, a digital x-ray detector, and a biopsy device, said programming instructions causing said control unit to operate said device to:
- acquire an x-ray exposure of the subject by irradiating the subject with x-rays from the x-ray source while the subject is interacting with the biopsy device, and detecting x-rays with said digital x-ray detector attenuated by the subject and said biopsy device, thereby generating digital data; and
- generate an image of the examination subject interacting with the biopsy device from said digital data, using image acquisition and image processing parameters determined from an x-ray exposure of the subject without interaction with the biopsy device.

* * * * *